(12) United States Patent
Schill et al.

(10) Patent No.: US 6,661,020 B2
(45) Date of Patent: Dec. 9, 2003

(54) SERVO-SHUTTER MECHANISM FOR DETECTING DEFECTS IN CANS

(75) Inventors: Joe Schill, Lynchburg, VA (US); Steve Walker, Goode, VA (US); Mark Plymale, Bedford, VA (US)

(73) Assignee: Delaware Capital Formation, Inc., Wilmington, DE (US)

( * ) Notice: Subject to any disclaimer, the term of this patent is extended or adjusted under 35 U.S.C. 154(b) by 148 days.

(21) Appl. No.: 09/941,630

(22) Filed: Aug. 30, 2001

(65) Prior Publication Data

US 2003/0042442 A1 Mar. 6, 2003

(51) Int. Cl.[7] ................................................. G03B 9/08
(52) U.S. Cl. ................... 250/559.45; 396/463; 250/229
(58) Field of Search ........................... 250/221, 559.45, 250/559.46, 559.47, 559.48, 559.49, 229, 232, 233; 396/463, 464, 469, 493, 497, 498

(56) References Cited

U.S. PATENT DOCUMENTS

| | | | | |
|---|---|---|---|---|
| 3,826,923 A | * | 7/1974 | Trimble et al. | 250/559.42 |
| 5,012,271 A | * | 4/1991 | Nishimura et al. | 396/234 |
| 5,307,110 A | * | 4/1994 | Sawabe et al. | 396/90 |
| 5,341,620 A | * | 8/1994 | Katou et al. | 53/287 |
| 5,365,298 A | * | 11/1994 | Fox | 396/453 |
| 5,798,531 A | * | 8/1998 | Harris | 250/559.03 |
| 6,384,421 B1 | * | 5/2002 | Gochar, Jr. | 250/559.46 |
| 6,493,513 B1 | * | 12/2002 | Noguchi et al. | 396/257 |
| 6,510,938 B1 | * | 1/2003 | Bowlin | 198/450 |

* cited by examiner

Primary Examiner—Stephone B Allen
(74) Attorney, Agent, or Firm—Foley & Lardner

(57) ABSTRACT

The present invention includes a servo-shutter mechanism comprising a servo-motor and a first gear rotatably attached to the servo-motor. The gear has teeth. The invention also includes a second gear having a first end and a second end. The first end has teeth in meshing contact with the teeth of the first gear and the second end is adapted to be joined to a cam ring. The cam ring has an aperture and a plurality of pivot pins where one of the pivot pins is joined to the second end of the second gear. Additionally, the invention includes at least one shutter blade having a first end and a second end where the first end is adapted to be pivotably joined to the cam ring and the second end is adapted to block the aperture.

19 Claims, 11 Drawing Sheets

SERVO-SHUTTER MECHANISM FOR DETECTING DEFECTS IN CANS

BACKGROUND OF THE INVENTION

A. Field of the Invention

The invention relates generally to a servo activated shutter mechanism and, more particularly, to a servo activated shutter mechanism adapted for use in can manufacturing.

B. Description of the Related Art

Manufacturing cans requires a large number of forming and machining operations. For example, fabrication of a two-piece beverage can may require two dozen or more separate necking, ironing, trimming, washing, decorating and spraying operations. Typically, these operations are performed in a series of modules by function. In any one of these operations, a can may be damaged and rendered unusable. If damaged, the can should be removed from the line to reduce the cost of manufacturing. Some processes include a mechanism to discharge such cans from the machine.

Prior to palletizing cans for shipment, all cans are individually inspected for pin holes, split flanges, split domes and other perforations. Some conventional systems use a light sensor. With the open end of the can seated and sealed up to the light sensor, the outside of the can is flooded with light. If there is a hole in the can, light will be admitted into the can and will be detected by the sensor. Thus, damaged cans can be identified and removed from the can-making line.

One conventional system uses a stand alone test machine after the final forming module. Cans are fed by traditional trackwork. Although this system works, each stand alone test machine requires a separate drive, control panel, conveyance and line controls. This adds a considerable cost to the manufacturing line.

Another conventional system, the positive transfer inspection machine, uses infeed and exit starwheels rather than traditional trackwork to feed and remove cans from the final forming modules. This system has the advantage that the light sensor is integrated into the module, obviating the need for the extra equipment required for the stand alone test machine.

Although more cost effective than the stand alone test machine, the positive transfer inspection machine has an inherent process drawback. It works well as long as there is a can in the pocket of the starwheel. However, if a can has already been removed from the upstream process (e.g. damaged can fallout), the sensor is exposed to an empty pocket. Therefore, the sensor is exposed to significantly more light than it is designed for. This results in the sensor being temporarily blinded. This is similar to what happens to the human eye when an individual is awakened at night from an overhead light. Typically, in the time it takes for the sensor to return to normal operation, as many as three cans or more may have passed by the sensor and be classified as having defects while in reality they may have been acceptable.

An empty pocket can be recognized in advance of the pocket reaching the light sensor by virtue of a proximity sensor. With the usage of an encoder or resolver, the time or position at which the pocket reaches the light sensor can be determined. However, the present state of light sensor technology does not allow the light sensor to "turn off" or "decay" fast enough relative to the upcoming adjacent empty pocket.

The required delay time is determined primarily by the machine speed and pocket-to-pocket pitch of the starwheels. A fast speed and small pitch combination on a positive transfer machine necessitates very fast decay times. However, current state of the art light sensors have decay times which are relatively slow, too slow for such combinations.

Thus, the prior art light testing apparatuses are easily blinded and are unsuitable for the rejection of defective cans in high speed positive transfer can manufacturing lines. Therefore, it would be desirable to have a light testing apparatus which is not easily blinded and acceptable for use in modern high speed can manufacturing.

SUMMARY OF THE INVENTION

The present invention includes a servo-shutter mechanism comprising a servo-motor, a first gear rotatably attached to the servo-motor, the gear having teeth, a second gear having a first end and a second end, the first end having teeth in meshing contact with the teeth of the first gear, and the second end adapted to be joined to a cam ring, a cam ring having an aperture and a plurality of pivot pins, one of the pivot pins joined to the second end of the second gear and at least one shutter blade having a first end and a second end, the first end adapted to be pivotably joined to the cam ring, the second end adapted to block the aperture.

The present invention also includes a light testing apparatus comprising a servo-motor, a first gear rotatably attached to the servo-motor, the gear having teeth, a second gear having a first end and a second end, the first end having teeth in meshing contact with the teeth of the first gear, the second end adapted to be joined to a cam a cam ring having an aperture and a plurality of pivot pins, one of said pivot pins joined to the second end of the second gear at least one shutter blade having a first end and a second end, the first end adapted to be pivotably joined to the cam ring, the second end adapted to block the aperture, a pin hole in the at least one shutter blade, the pin hole adapted to admit a predetermined amount of light, a light source adapted to shine light onto a container and a light sensor adapted to detect the predetermined light.

Additionally, the present invention includes a method of testing a can for defects comprising the steps of conveying the can to a light detecting apparatus, the apparatus including a servo-motor, a first gear rotatably attached to the servo-motor, the gear having teeth, a second gear having a first end and a second end, the first end having teeth in meshing contact with the teeth of the first gear and the second end adapted to be joined to a cam ring, the cam ring having an aperture and a plurality of pivot pins, one of said pivot pins joined to the second end of the second gear and at least one shutter blade having a first end and a second end, the first end adapted to be pivotably joined to the cam ring, the second end adapted to block the aperture, shining light onto the can and detecting light from the can with the light detecting mechanism.

The present invention also includes a method for testing cans for defects comprising the steps of determining if a pocket in a can conveying apparatus is empty, substantially preventing light from a light source from impinging on a light sensor if the pocket is empty and if the pocket is full, opening a path capable of allowing light from the light source to the light sensor. The step of determining if a pocket in a can conveying apparatus is empty may be done with a proximity sensor.

BRIEF DESCRIPTION OF THE DRAWINGS

The foregoing advantages and features of the invention will become apparent upon reference to the following detailed description and the accompanying drawings, of which.

DETAILED DESCRIPTION OF SPECIFIC EMBODIMENTS

The present inventors have discovered several features which result in a light testing apparatus which is not easily blinded by an empty pocket of a starwheel. These features provide a light tester which is sensitive yet robust enough for use in modern high speed can manufacturing. These features include a high speed servo-motor controlling a shutter mechanism, a pin hole in at least one shutter blade and a proximity sensor.

Figure 1:
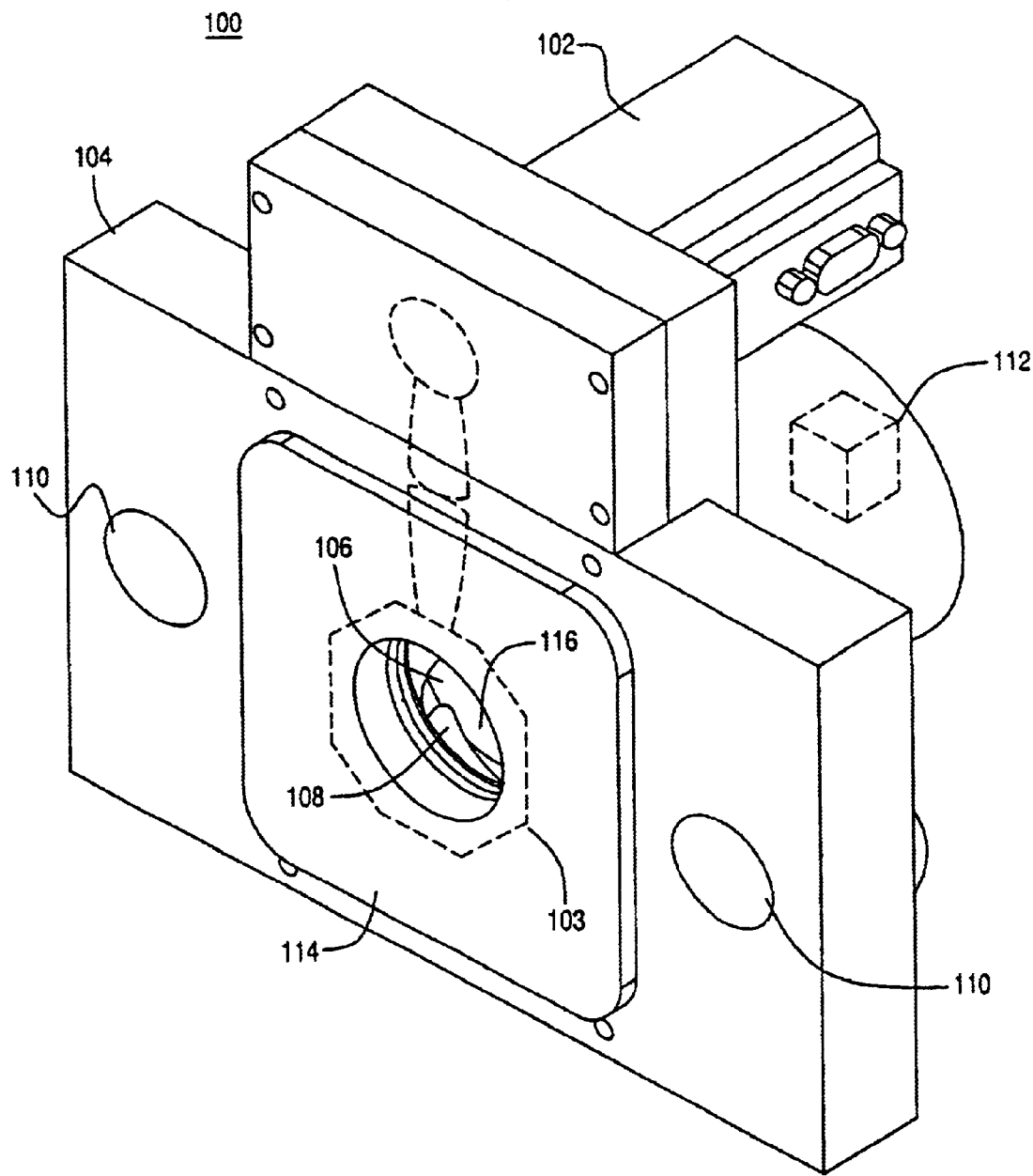
FIG. 1 is a perspective view of the front of the first embodiment of the invention.
Figure 2:
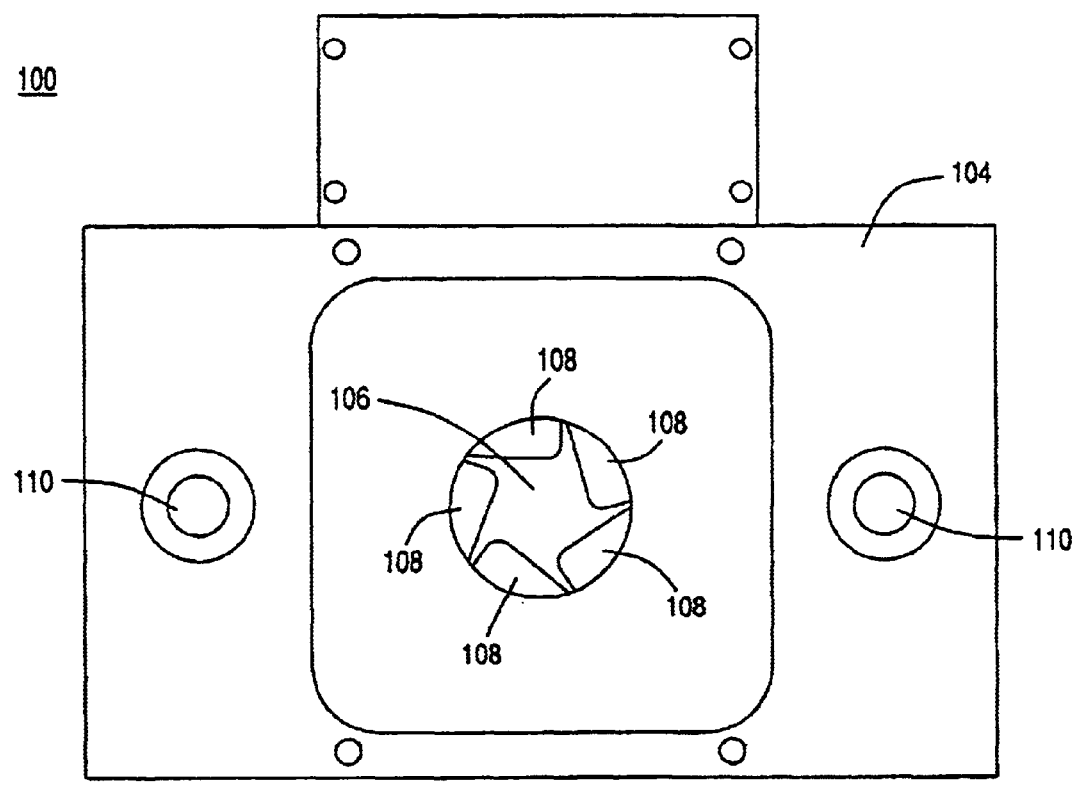
FIG. 2 is a front view of the first embodiment of the invention.
Figure 3:
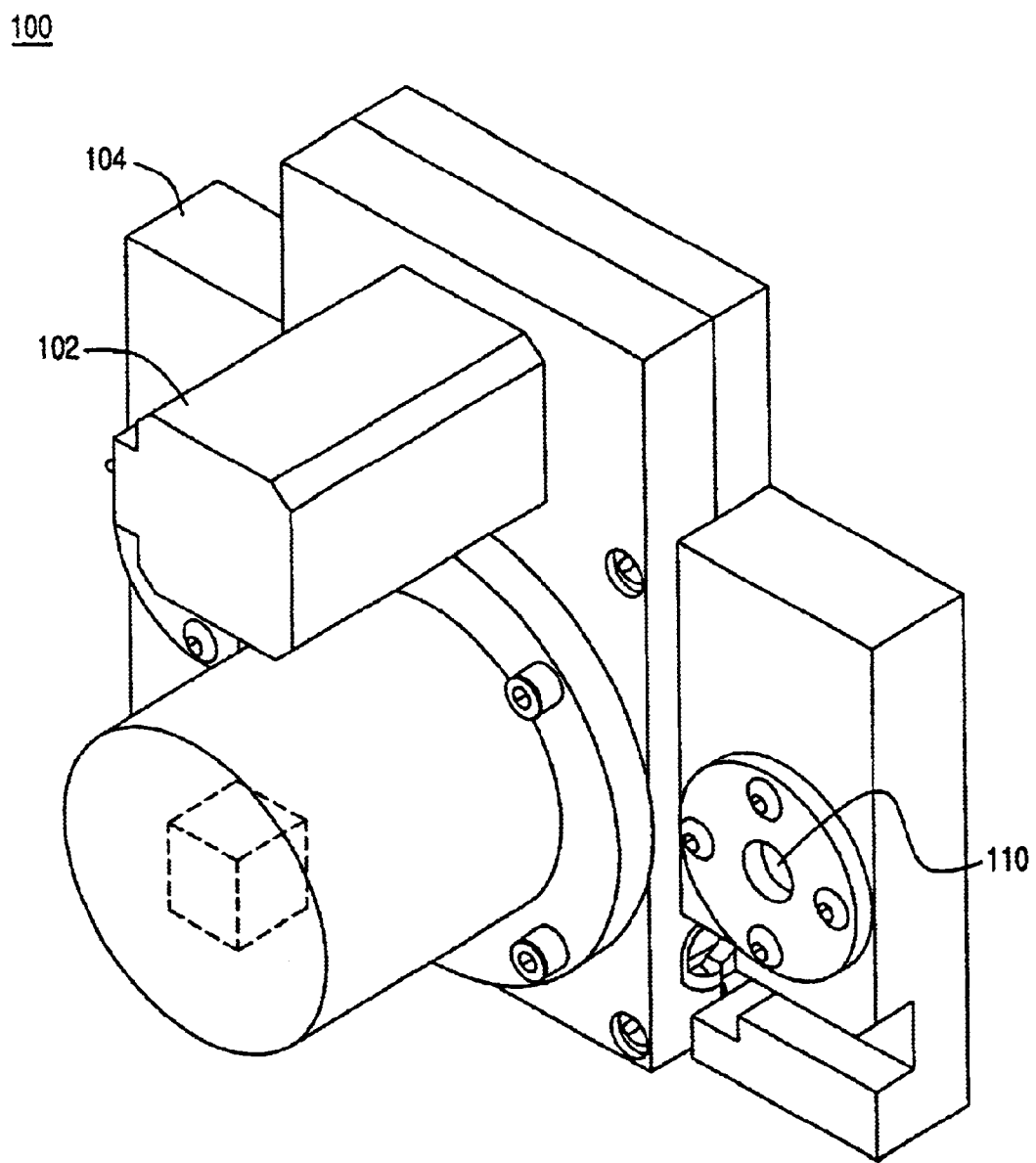
FIG. 3 is a perspective view of the rear of the first embodiment of the invention.
Figure 4:
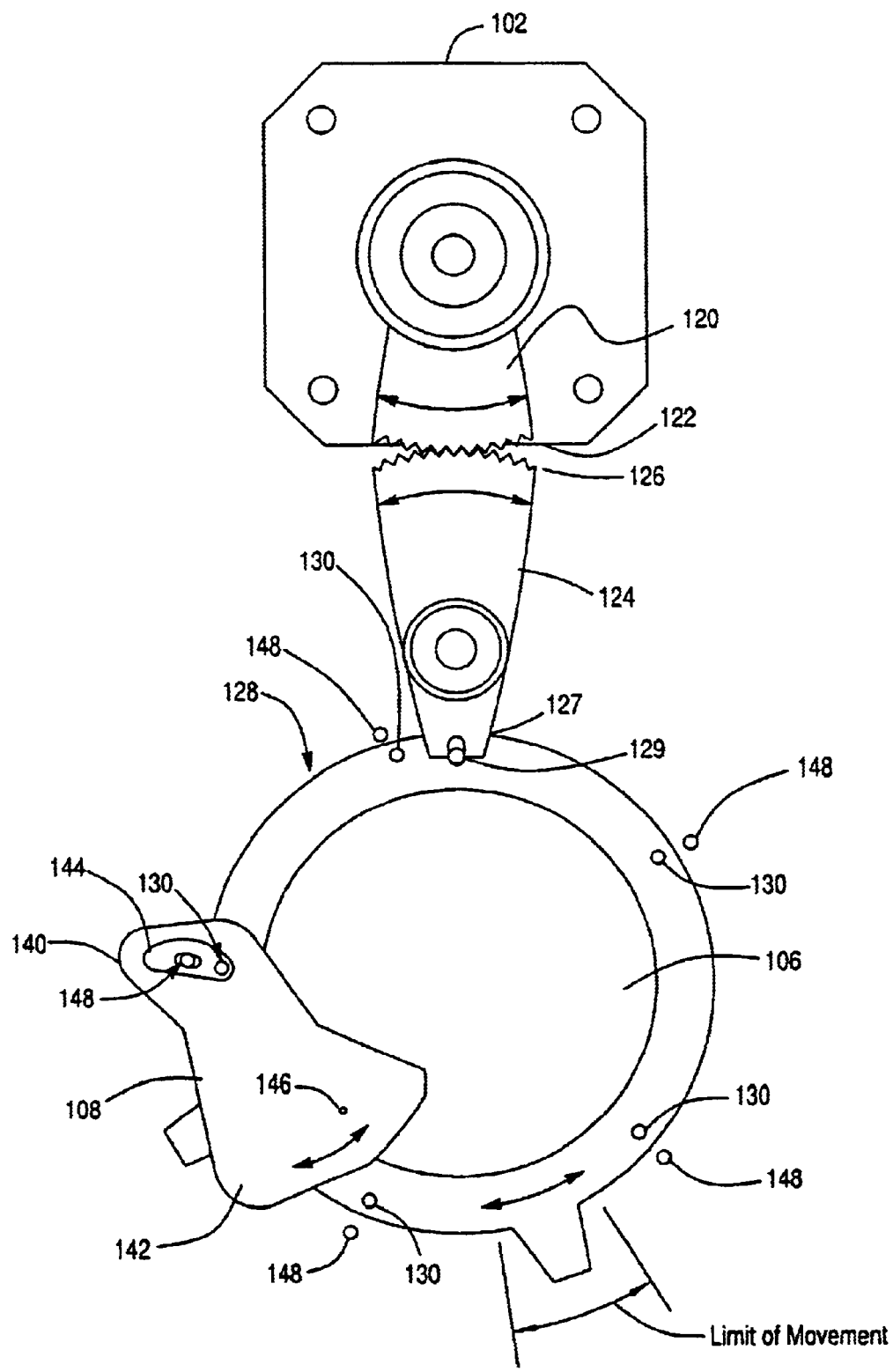
FIG. 4 is a partial view of the first embodiment of the invention.
Figure 5:
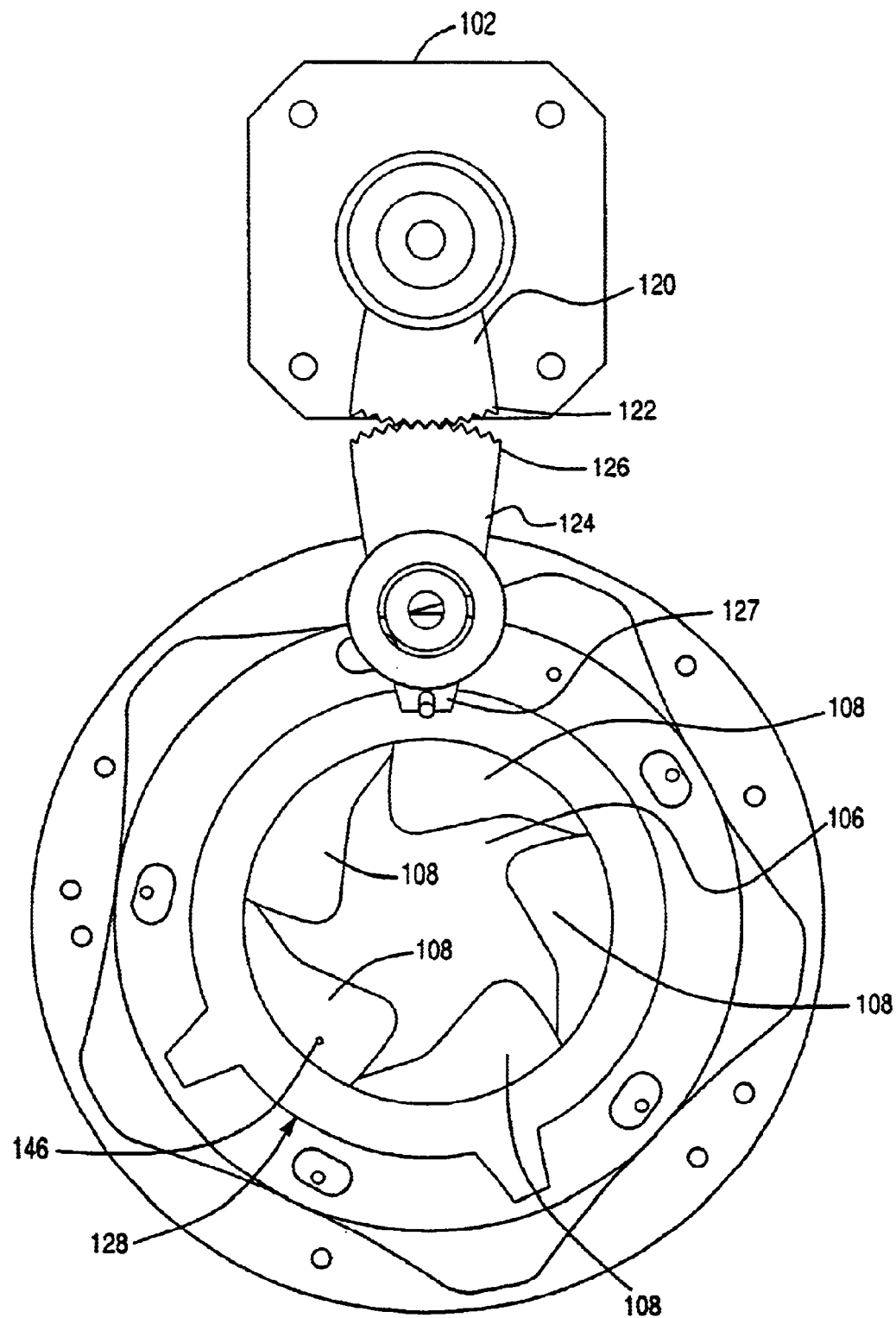
FIG. 5 is a partial view of the first embodiment of the invention.
Figure 6:
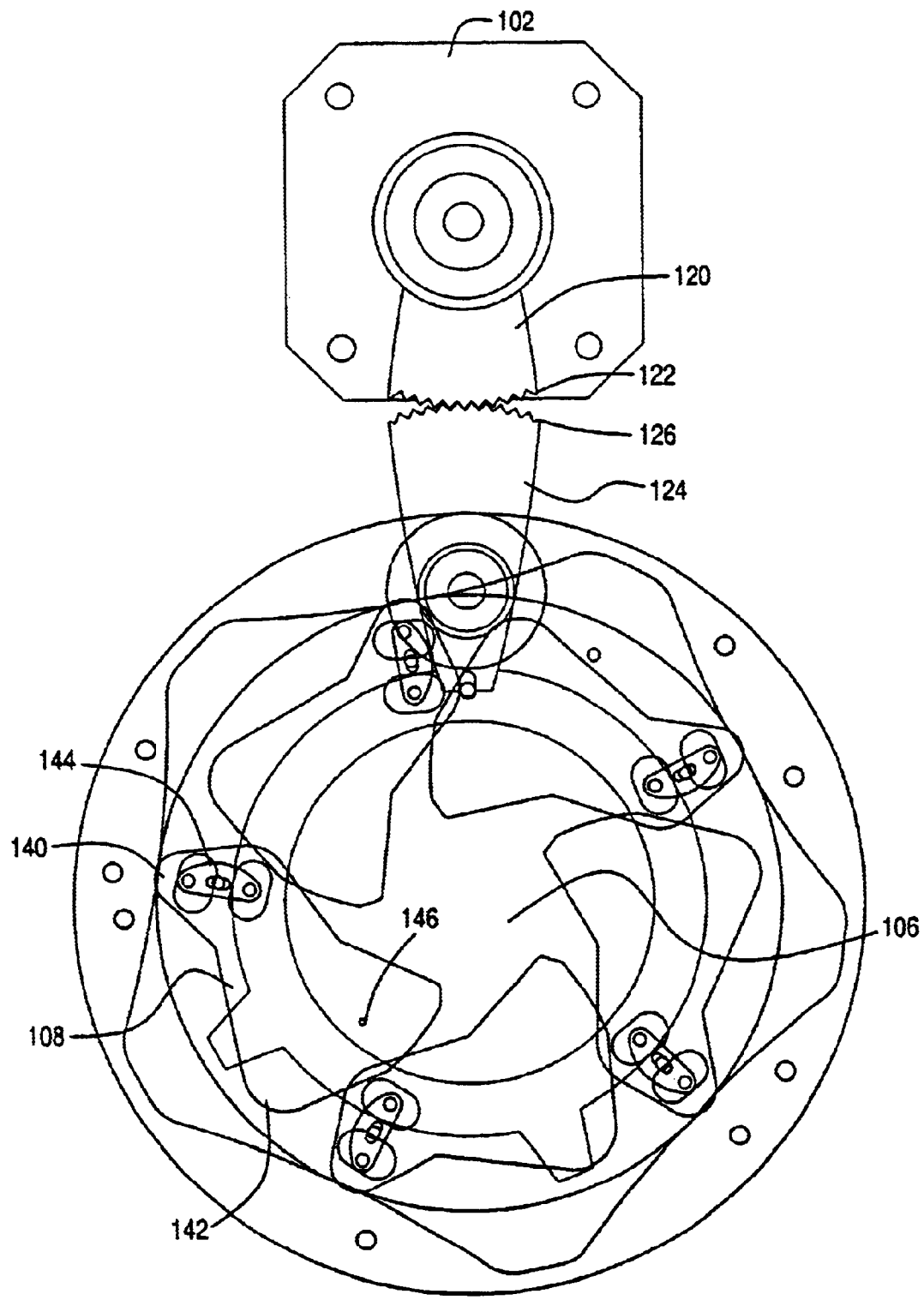
FIG. 6 a partial view of the first embodiment of the invention.
Figure 7:
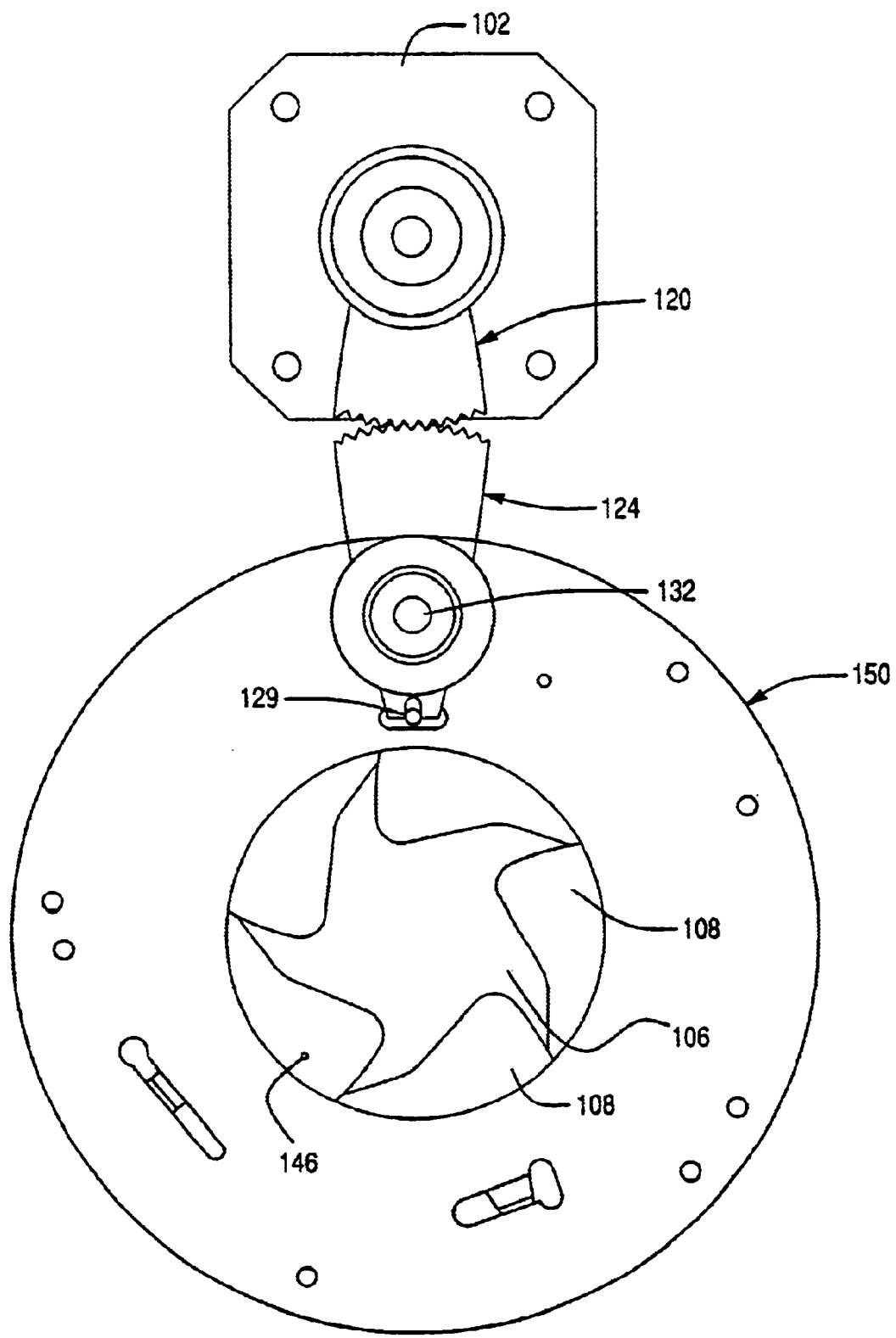
FIG. 7 a partial view of the first embodiment of the invention.

FIGS. 1 and 2 illustrate front views of the first embodiment of the invention while FIG. 3 is a rear view. The servo-shutter mechanism 100 comprises a servo-motor 102 and a shutter mechanism 103 (discussed in more detail below) enclosed in a housing 104. On the front of the housing is a face plate 114 with an opening 116. Light enters the shutter mechanism through opening 116 and passes through the shutter aperture 106 to a light sensor 112. Although the size of the aperture 106 can be varied, typically it is either open or shut. The aperture 106 is opened and closed with shutter blades 108. Additionally, the housing 104 has two mounting holes 110 which can be used to mount the shutter mechanism.

FIGS. 4–7 are partial cutaway views of the first embodiment of the invention and will be used to describe the construction and operation of the embodiment. Rotatably attached to the servo-motor 102 is a drive gear 120. The actual amount of rotation required to operate the shutter mechanism 103 is relatively small. Thus, in the preferred embodiment illustrated in FIG. 4, a large portion of the drive gear 120 has been cut off. By eliminating a large portion of the drive gear 120, the speed of the shutter mechanism 103 is significantly increased.

Meshing with the tooth portion 122 of the drive gear 120 is a tooth portion 126 of a shutter gear 124. Shutter gear 124 is rotatably affixed to cover plate 150 (FIG. 7) via attachment pin 132. Preferably, attachment pin 132 includes a bushing (not shown). Opposite to the tooth portion 126, the shutter gear 124 has a drive portion 127. The drive portion 127 is affixed to a drive pin 129 on a cam ring 128.

In the preferred embodiment of the invention, there are five shutter blades 108 pivotably attached to the cam ring. However, any number of shutter blades 108 may be used. The shutter blades 108 have a have an attachment portion 140 and a blade portion 142. The attachment portion 140, in one embodiment, includes a pivot slot 144. The pivot slot 144 fits over a pivot pin 130 provided on the cam ring 128 (see FIG. 4). The pivot slot 144 also fits over a fixed pivot point 148 fastened to a fixed plate (not shown).

When the drive gear rotates clockwise in the figures, it drives the shutter gear counterclockwise. The drive portion 127 of the shutter gear 124 pulls on the attachment pin 129 of the cam ring 128. This causes the cam ring 128 to rotate in the clockwise direction. This, in turn, causes the shutter blades 108 to pivot in a counterclockwise direction. In this manner, the aperture 106 in the cam ring 128 is covered by the blade portion 142 of blades 108. By rotating the drive gear 120 in the counterclockwise direction, the process is reversed and the aperture 106 is opened.

Additionally, included in at least one of the shutter blades 108 is a pin hole 146. This pin hole 146 allows a predetermined amount of light into the shutter mechanism. The pin hole 146 may be used to test both the sensor and each pocket's ability to pass light. In addition, the pin hole test may be used to check for light leakage and aid in calibration of the system. Covering and protecting the attachment portion 140 of blades 108 and the cam ring 128 is a cover plate 150.

FIGS. 8 to 12 illustrate a light testing apparatus 200 according to the present invention. In this embodiment, the servo-shutter mechanism 100 is mounted in housing 210. Cans are delivered from the previous forming operation via transfer starwheel 206 to the main turret 202. As the cans proceed under the light 204, a pusher pad 216 advances the can against a seal 214. The seal 214 is preferably made of rubber, however, the seal made be made of any suitable material. A proximity sensor 218 mounted on the side of housing 221, which supports the transfer starwheel 206 detects if there is a can in the pocket of the main turret 202 or transfer starwheel 206. If the pocket is empty, an electronic circuit (not shown) activates the servo-shutter mechanism 100 and closes the aperture 106 before the specific pocket reaches the servo-shutter mechanism 100 but after its prior adjacent pocket is inspected. In this way, the sensor 112 is prevented from being blinded. If the proximity sensor 218 detects a can in the following pocket, a signal is sent to the servo-shutter mechanism 100 to open the aperture 106 to inspect the next pocket.

Figure 9:
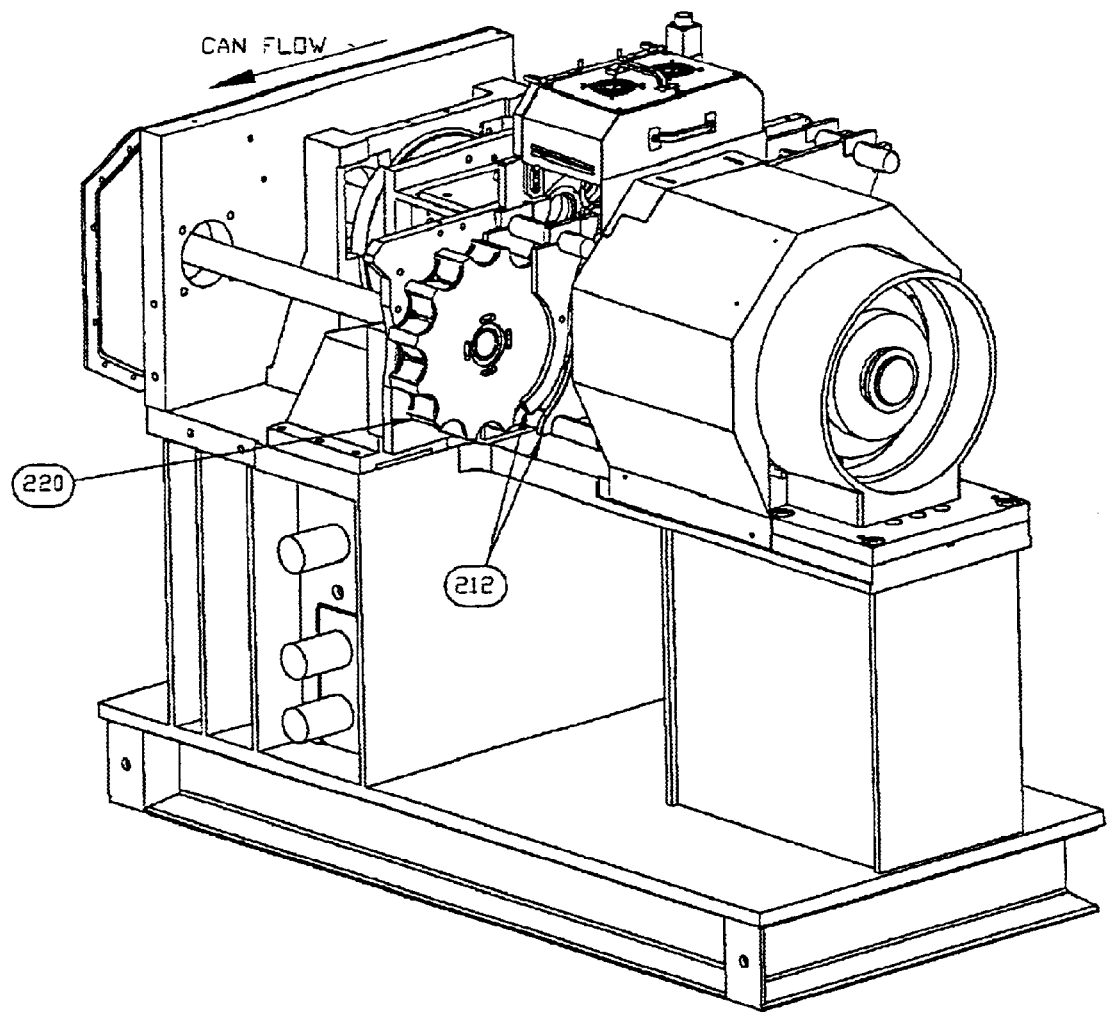
FIG. 9 is a perspective view from the exit side of the second embodiment of the invention.

If there is a can in the pocket of the main turret 202, the aperture 106 is in the open position. With the can sealed against the seal 214, no light can reach the sensor 112 unless the can has pins holes, split flanges, split domes or other perforations. If the sensor detects one of these defects a signal is sent to a controller (not shown) which activates a rejection device 212 (FIG. 9). In the preferred embodiment of the invention, the rejection device 212 comprises an air jet which blows the reject can off the exiting transfer starwheel 220. Mechanical devices would work equally as well.

Figure 8:
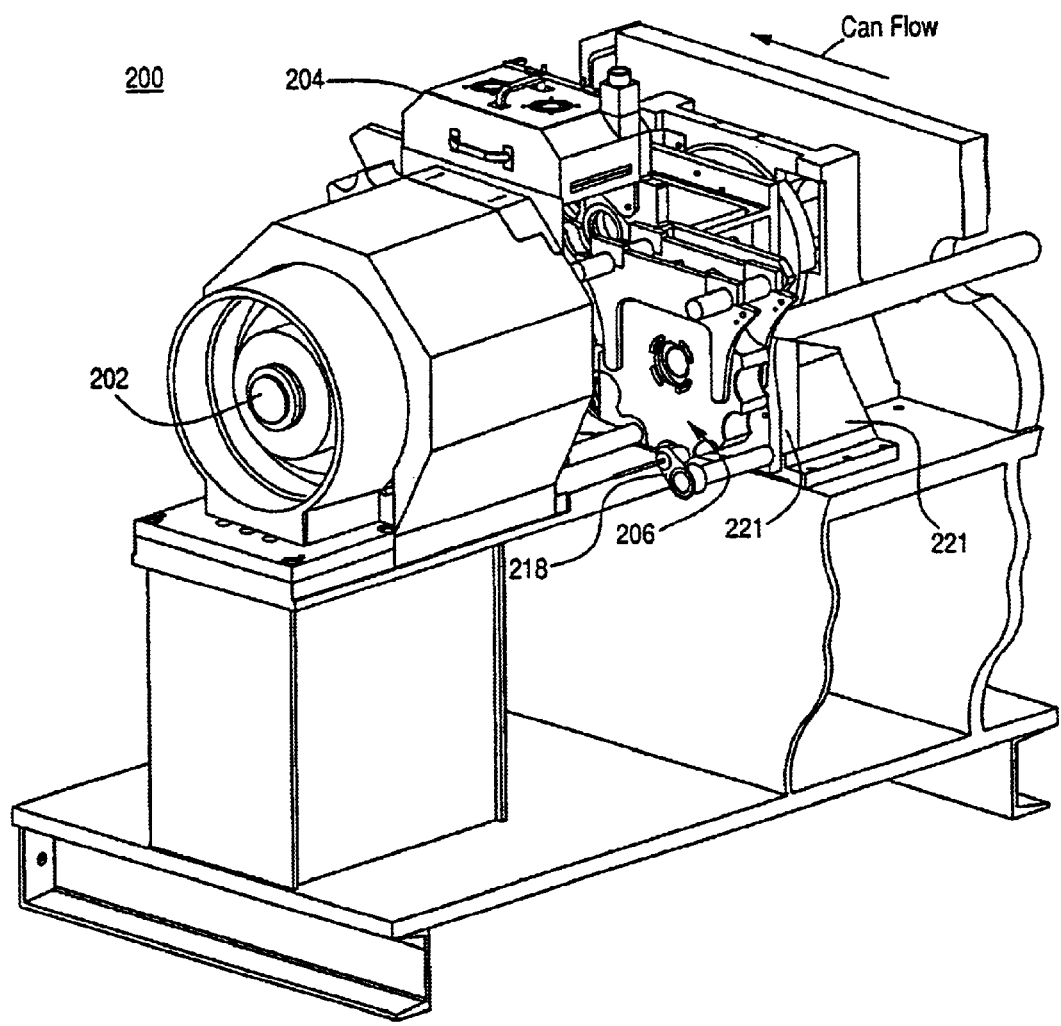
FIG. 8 is a perspective view from the infeed side of the second embodiment of the invention.
Figure 10:
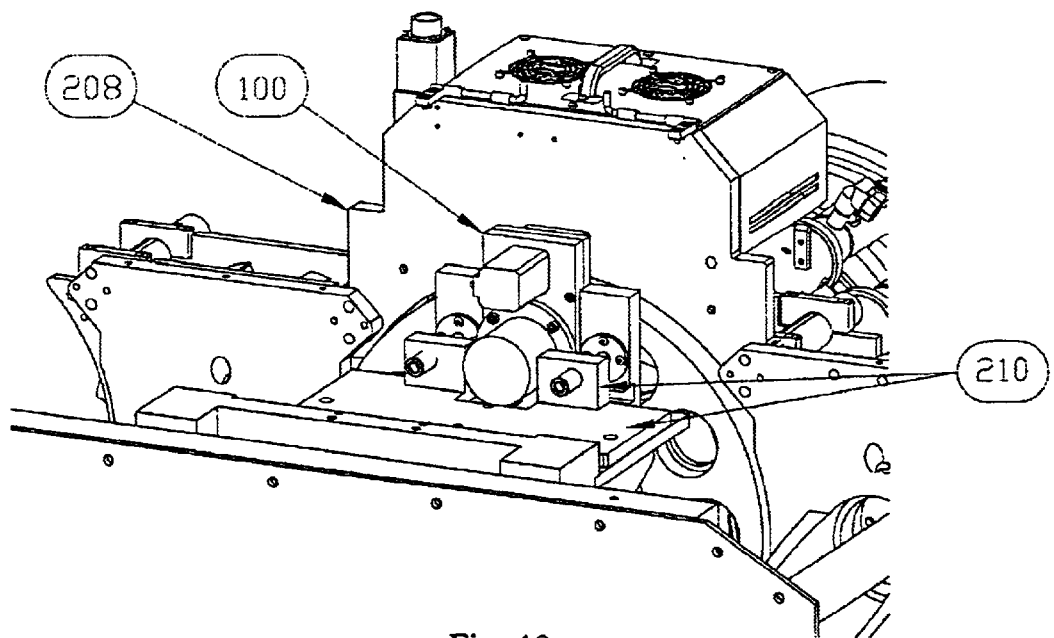
FIG. 10 is a perspective view from the sensor side of the second embodiment of the invention.
Figure 11:
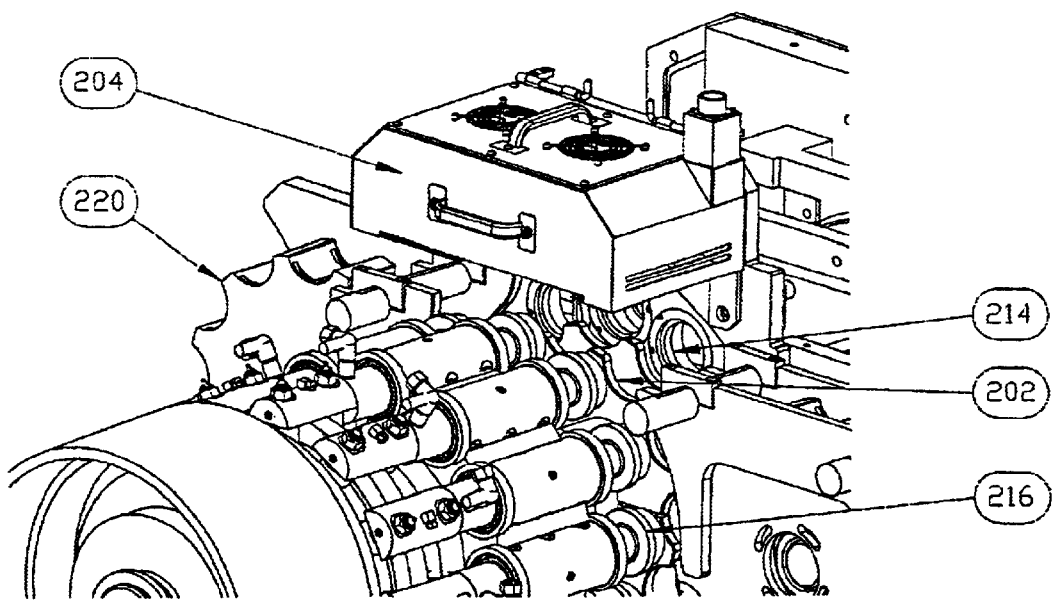
FIG. 11 is a perspective view from the pusher side of the second embodiment of the invention.
Figure 12:
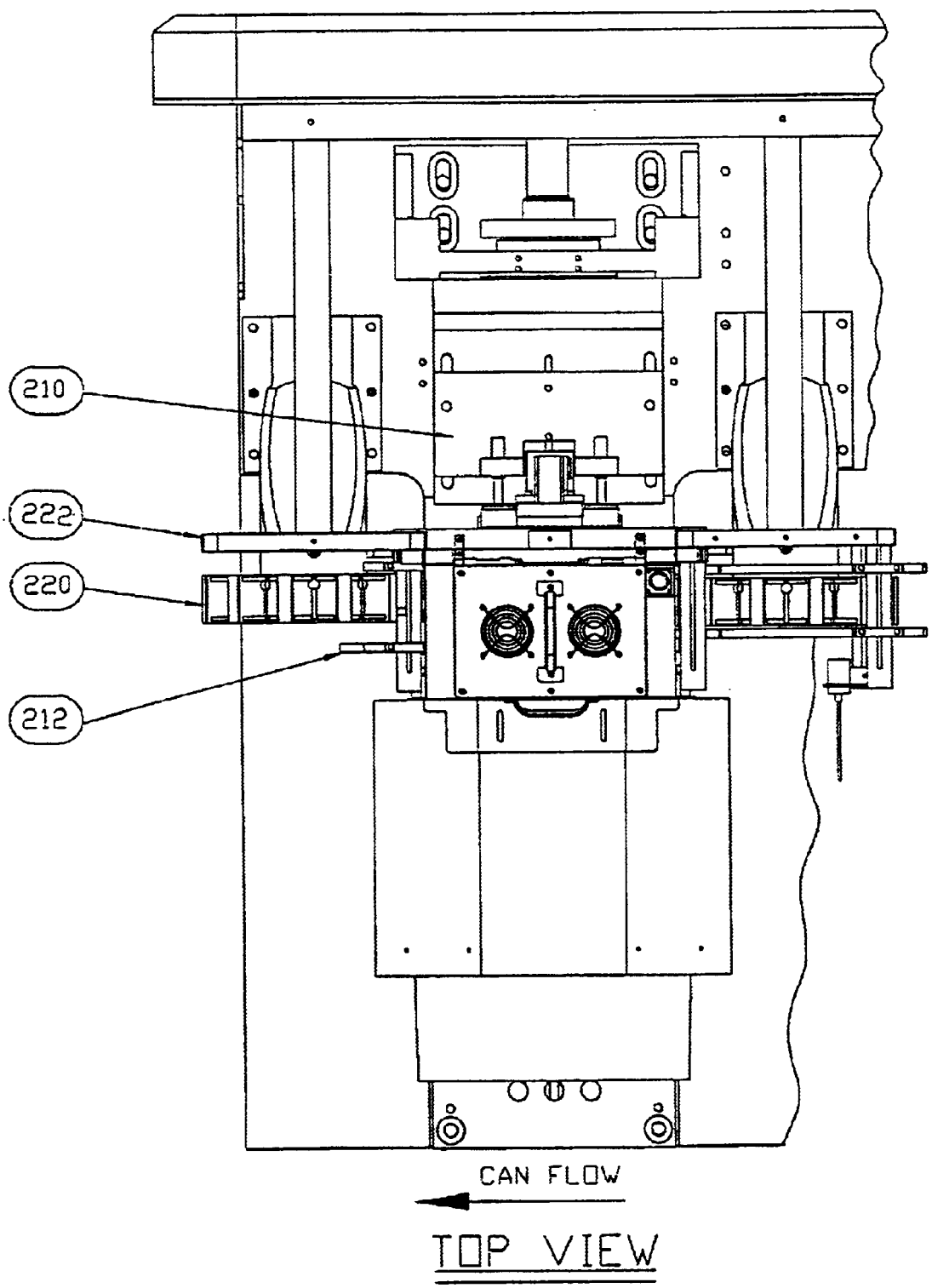
FIG. 12 is a plan view of the second embodiment of the invention.

As illustrated in the embodiment in FIGS. 8 and 10, the light source 204, is a light assembly attached to the machine frame 208. However, in another aspect of the invention a light assembly is mounted to the turret guard 222. In still another aspect, the light source 204 is a free standing lamp. The light source 204 may comprises ordinary incandescent bulbs, halogen bulbs, fluorescent bulbs or any other light source generating suitable light for the sensor 112.

Thus, a servo-shutter mechanism, light testing apparatus and method of using the same has been described according to the present invention. Many modifications and variations may be made to the techniques and structures described and illustrated herein without departing from the spirit and scope of the invention. Accordingly, it should be understood that the methods and apparatus described herein are illustrative only and are not limiting upon the scope of the invention.

What is claimed is:

1. A servo-shutter mechanism comprising:
   a servo-motor;
   a first gear rotatably attached to the servo-motor, the gear having teeth;
   a second gear having a first end and a second end, the first end having teeth in meshing contact with the teeth of the first gear, and the second end adapted to be joined to a cam ring;
   a cam ring having an aperture and a plurality of pivot pins, one of said pivot pins joined to the second end of the second gear; and
   at least one shutter blade having a first end and a second end, the first end adapted to be pivotably joined to the cam ring, the second end adapted to block the aperture.

2. A servo-shutter mechanism according to claim 1, further comprising a pin hole in one shutter blade, the pin hole adapted to admit a predetermined amount of light.

3. A servo-shutter mechanism according to claim 1, further comprising a plurality of shutter blades.

4. A light testing apparatus comprising:
   a servo-motor;
   a first gear rotatably attached to the servo-motor, the gear having teeth;
   a second gear having a first end and a second end, the first end having teeth in meshing contact with the teeth of the first gear, the second end adapted to be joined to a cam;
   a cam ring having an aperture and a plurality of pivot pins, one of said pivot pins joined to the second end of the second gear;
   at least one shutter blade having a first end and a second end, the first end adapted to be pivotably joined to the cam ring, the second end adapted to block the aperture;
   a pin hole in the at least one shutter blade, the pin hole adapted to admit a predetermined amount of light;
   a light source adapted to shine light onto a container; and
   a light sensor adapted to detect the predetermined light.

5. The apparatus of claim 4, further comprising a plurality of shutter blades.

6. The apparatus of claim 4, further comprising a turret to pass containers past the light source.

7. The apparatus of claim 6, further comprising turret guards.

8. The apparatus of claim 7, further comprising a machine frame and wherein the light source is installed on the machine frame.

9. The apparatus of claim 6, further comprising a rejection apparatus for ejecting rejected containers from the turret.

10. The apparatus of claim 9, wherein the rejection apparatus comprises an air jet.

11. A method of testing a can for defects comprising the steps of:
    conveying the can to a light detecting apparatus, the apparatus including a servo-motor, a first gear rotatably attached to the servo-motor, the gear having teeth, a second gear having a first end and a second end, the first end having teeth in meshing contact with the teeth of the first gear and the second end adapted to be joined to a cam ring, the cam ring having an aperture and a plurality of pivot pins, one of said pivot pins joined to the second end of the second gear and at least one shutter blade having a first end and a second end, the first end adapted to be pivotably joined to the cam ring, the second end adapted to block the aperture;
    shining light onto the can; and
    detecting light from the can with the light detecting apparatus.

12. The method of claim 11, further comprising the step of sealing the can to eliminate ambient and process light.

13. The method of claim 11, wherein the defects are selected from the group consisting of pin holes, split flanges, split domes and perforations.

14. The method of claim 11, further comprising the step of rejecting a can which emits light higher than a predetermined amount.

15. The method of claim 11, wherein the step of conveying comprises using a turret with pockets.

16. The method of claim 15, further comprising the step of determining if a pocket is empty prior to the step of detecting light at that pocket position.

17. The method of claim 16, further comprising the step of closing the at least one shutter blade prior to the step of detecting if the pocket is empty at that pocket position.

18. The method of claim 17, further comprising the step of opening the at least one shutter blade after the empty pocket passes the light detecting apparatus.

19. The method of claim 18, wherein the step of opening the at least one shutter blade occurs after the last of a plurality of empty pockets in succession.

* * * * *